United States Patent [19]
Tice et al.

[11] Patent Number: 5,629,264
[45] Date of Patent: May 13, 1997

[54] 2-ARYL-5,6-DIHYDROPYRIMIDINONES AND HERBICIDAL USE THEREOF

[75] Inventors: Colin M. Tice, Elkins Park; Lois M. Bryman, North Wales; Renee C. Roemmele, Maple Glen, all of Pa.

[73] Assignee: Rohm and Haas Company, Philadelphia, Pa.

[21] Appl. No.: 409,293

[22] Filed: Mar. 23, 1995

[51] Int. Cl.⁶ ............................ A01N 43/54; C07D 239/06
[52] U.S. Cl. ............... 504/240; 504/242; 504/243; 544/253; 544/283; 544/284; 544/319
[58] Field of Search ............... 514/258, 259, 514/269; 544/253, 283, 284, 319; 504/242, 240, 243

[56] References Cited

U.S. PATENT DOCUMENTS

| | | | |
|---|---|---|---|
| 4,113,868 | 9/1978 | Bernath et al. | 544/253 |
| 4,431,440 | 2/1984 | Bhalla et al. | 504/240 |
| 4,771,040 | 9/1988 | Maurer et al. | 514/86 |
| 5,300,477 | 4/1994 | Tice | 504/242 |
| 5,453,414 | 9/1995 | Tice et al. | 504/133 |

FOREIGN PATENT DOCUMENTS 0058822  9/1982  European Pat. Off. .

OTHER PUBLICATIONS

J. Org. Chem, 1993, 58, 4490–4493.

*Primary Examiner*—Yogendra N. Gupta
*Attorney, Agent, or Firm*—Clark R. Carpenter

[57] ABSTRACT

A class of 2-aryl-5,6-dihydropyrimidinones and compositions thereof which are useful in the control of weeds is of the general formula

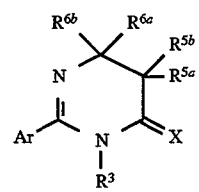

wherein Ar is a substituted or unsubstituted aryl or heteroaryl;
$R^3$ is an optionally substituted alkyl, alkenyl or alkynyl;
$R^{5a}$ and $R^{5b}$ are each independently a hydrogen atom, halo, cyano or an optionally substituted alkyl, alkenyl, alkynyl, alkoxy or alkylthio;
$R^{6a}$ and $R^{6b}$ are each independently a hydrogen atom, halo, cyano, an optionally substituted alkyl, alkenyl, alkynyl, alkoxy or alkylthioalkyl, cycloalkyl, optionally substituted aryl, aryloxy, heterocyclyl or aralkyl, alkylamino, dialkylamino or dialkylaminocarbonyl;
$R^{5a}$ and $R^{6a}$ taken together with the carbon atoms to which they are attached may form a fused 4–7 member ring containing 2–5 methylenes; and
X is an oxygen or a sulfur atom.

22 Claims, No Drawings

2-ARYL-5,6-DIHYDROPYRIMIDINONES AND HERBICIDAL USE THEREOF

The need continues for novel and improved herbicidal compounds and compositions. This is particularly so since the targets of herbicides can become resistant to known herbicides over time and after use of such compositions. Additionally, economic and environmental considerations can favor herbicides having different modes of performance than those currently used. This invention relates to novel 2-aryl-5,6-dihydropyrimidinones, compositions comprising 2-aryl5,6-dihydropyrimidinones, and the use of 2-aryl-5,6-dihydropyrimidinones and compositions thereof as broad spectrum herbicides which are effective against both monocot and dicot weed species in either preemergence or postemergence applications. This invention also teaches methods of preparing these compounds as well as methods of using the compounds as herbicides.

Veale et al. in *J. Org. Chem.*, 58, 4990–4993 (1993) disclose certain 2-aryl-5,6-dihydropyrimidinone compounds, useful as nonpeptidic inhibitors of the enzyme human leukocyte elastase, which are substituted at the 3-position with an alkyl or a dialkoxyalkyl group. No pesticidal utility is suggested.

Bernath et al. in U.S. Pat. No. 4,113,868 disclose certain 2,3-diaryl-5,6-dihydropyrimidinone compounds, useful as anti-inflamatory, antifebrile, analgesic and narcosis potentiators, which are substituted at the 5,6-positions by a methylene link to form a fused 5–7 member ring. No pesticidal utility is suggested.

Tice in U.S. Pat. No. 5,300,477 discloses certain 2-arylpyrimidinones which are useful in the control of weeds. No teaching or suggestion is present concerning the use of 2-aryl-5,6-dihydropyrimidinones and compositions thereof as broad spectrum herbicides.

This invention relates to 2-aryl-5,6-dihydropyrimidinone compounds having the general formula

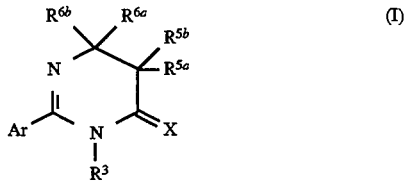

wherein

Ar is a substituted or unsubstituted aryl or heteroaryl;

$R^3$ is a haloalkyl, polyhaloalkyl, alkenyl, haloalkenyl, polyhaloalkenyl, alkynyl, haloalkynyl, polyhaloalkynyl, alkenynyl, alkoxyalkyl, haloalkoxyalkyl, oxoalkyl, trimethylsilylalkynyl or cyanoalkyl;

$R^{5a}$ and $R^{5b}$ are each independently a hydrogen atom, halo, alkyl, alkenyl, alkynyl, alkoxy, alkylthio, alkoxycarbonyl, alkoxycarbonylalkyl, haloalkyl, haloalkenyl, haloalkynyl, haloalkoxy, polyhaloalkyl, polyhaloalkenyl, polyhaloalkynyl, polyhaloalkoxy, trimethylsilylalkynyl or cyano;

$R^{6a}$ and $R^{6b}$ are each independently a hydrogen atom, halo, alkyl, alkenyl, alkynyl, alkoxy, alkylthio, haloalkylthio, alkoxyalkyl, alkoxycarbonyl, alkoxycarbonylalkyl, haloalkyl, haloalkoxy, haloalkenyl, haloalkynyl, polyhaloalkyl, polyhaloalkoxy, polyhaloalkylthio, polyhaloalkenyl, polyhaloalkynyl, cycloalkyl, aryl, aryloxy, heterocyclyl, aralkyl, alkylamino, dialkylamino, dialkylaminocarbonyl or cyano;

$R^{5a}$ and $R^{6a}$ taken together with the carbon atoms to which they are attached may form a fused 4–7 member ring containing 2–5 methylenes; and X is an oxygen or a sulfur atom.

More particularly in this aspect of this invention, Ar is furyl, phenyl, naphthyl, pyridyl or thienyl, or furyl, phenyl, naphthyl, pyridyl or thienyl substituted with up to three substituents independently selected from bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl, polyhalo$(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, hydroxyimino, polyhalo$(C_1-C_{12})$alkoxy and nitro.

Preferred phenyl groups are phenyl, 3-methylphenyl, 3-methoxyphenyl, 3-nitrophenyl, 4-fluorophenyl, 4-chlorophenyl, 3trifluoromethylphenyl, 3-bromophenyl, 3-chlorophenyl, 3-fluorophenyl, 3trifluoromethoxyphenyl, 3-cyanophenyl, 3-(1,3-dioxolan-2-yl)phenyl, 3(hydroxyimino)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, and 3,4,5-trifluorophenyl. More preferred phenyl groups are phenyl, 3-fluorophenyl, 3,5-difluorophenyl, 3,5-dichlorophenyl and 3-chlorophenyl.

Preferred pyridyl groups are 6-chloro-2-pyridyl, 3-pyridyl, 5-bromo-3pyridyl, 5,6-dichloro-3-pyridyl, 5-chloro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4-pyridyl and 2,6-dichloro-4-pyridyl. More preferred pyridyl groups are 2-chloro-4-pyridyl, 2-fluoro-4-pyridyl, 5-chloro-3pyridyl and 2,6-dichloro-4-pyridyl.

Preferred furyl groups are 2-furyl and 3-furyl.

A preferred naphthyl group is 2-naphthyl.

Preferred thienyl groups are 2-thienyl, 3-thienyl, 4-chloro-2-thienyl, 5-chloro-2-thienyl, 5-chloro-3-thienyl and 2,5-dichloro-3-thienyl. A more preferred thienyl group is 5-chloro-3-thienyl.

$R^3$ is halo$(C_1-C_3)$alkyl, polyhalo$(C_1-C_3)$alkyl, $(C_3-C_4)$alkenyl, halo$(C_3-C_4)$alkenyl, polyhalo$(C_3-C_4)$alkenyl, $(C_3-C_6)$alkynyl, halo$(C_3-C_6)$alkynyl, polyhalo$(C_3-C_6)$alkynyl, $(C_5-C_6)$alkenynyl, $(C_1-C_6)$alkoxy$(C_1-C_6)$alkyl, halo$(C_1-C_6)$alkoxy$(C_1-C_6)$alkyl, 2-oxo$(C_2-C_3)$alkyl, trimethylsilyl$(C_3-C_4)$alkynyl or cyano$(C_1-C_6)$alkyl.

Preferred alkenyl and haloalkenyl groups are $(C_3-C_4)$ alkenyls and halo$(C_3-C_4)$alkenyls. More preferred are allyl and 3-chloroallyl.

Preferred alkynyl groups are $(C_3-C_6)$alkynyl. More preferred are pentynyl, propargyl and 2-butynyl. Most preferred alkynyl groups are 2-pentynyl, propargyl, and 2-butynyl.

Preferred halo substituted $(C_3-C_6)$alkynyl groups are halo $(C_3-C_4)$alkynyl. More preferred are iodopropargyl and bromopropargyl.

Preferred $(C_1-C_6)$alkoxy$(C_1-C_6)$alkyls are (C1-C2) alkoxy$(C_1-C_3)$alkyl. More preferred are methoxymethyl and 2-methoxyethyl. Most preferred is methoxymethyl.

A preferred 2-oxo$(C_2-C_3)$alkyl is acetonyl.

A preferred trimethylsilyl $(C_3-C_4)$alkynyl is 3(trimethylsilyl)propargyl.

A preferred $(C_5-C_6)$alkenynyl is pent-4-en-2-ynyl.

A preferred cyano $(C_1-C_6)$alkyl is cyanomethyl.

$R^{5a}$ and $R^{5b}$ are each independently a hydrogen atom, $(C_1-C_6)$alkyl, $(C_2-C_6)$alkenyl, $(C_2-C_6)$alkynyl, trimethylsilyl($C_2$-$C_3$)alkynyl, ($C_1$-C6)alkoxy, halo($C_1$-$C_6$) alkyl, polyhalo($C_1$-$C_6$)alkyl, halo($C_2$-$C_6$)alkenyl, polyhalo ($C_2$-$C_6$)alkenyl, halo($C_2$-$C_6$)alkynyl, polyhalo($C_2$-$C_6$) alkynyl, halo($C_1$-$C_6$)alkoxy, polyhalo($C_1$-$C_6$)alkoxy, ($C_1$-$C_6$)alkoxycarbonyl, ($C_1$-$C_3$)alkoxycarbonyl($C_1$-$C_3$) alkyl, ($C_1$-$C_6$)alkylthio, halo or cyano.

Preferred (C-$C_6$)alkyls are methyl, ethyl, n-propyl and isopropyl. More preferred are methyl and ethyl.

Preferred ($C_2$-$C_6$)alkynyls are ($C_2$-$C_3$)alkynyls. More preferred is propargyl.

Preferred ($C_1$-$C_6$)alkoxys are ($C_1$-$C_2$)alkoxys. More preferred is methoxy.

Preferred ($C_1$-$C_6$)alkylthios are ($C_1$-$C_2$)alkylthios. More preferred is methylthio.

Preferred ($C_1$-$C_6$)alkoxycarbonyls are ($C_1$-$C_3$) alkoxycarbonyls. More preferred are methoxycarbonyl and ethoxycarbonyl.

A preferred ($C_1$-$C_3$)alkoxycarbonyl($C_1$-$C_3$)alkyl is methoxycarbonylmethyl.

Preferred ($C_2$-$C_6$)alkenyls are ($C_2$-$C_3$)alkenyls. More preferred is allyl.

Preferred halo($C_1$-$C_6$)alkyls and polyhalo($C_1$-$C_6$)alkyls are halo($C_1$-$C_2$)alkyls and polyhalo($C_1$-$C_2$)alkyls. More preferred are fluoromethyl and trifluoromethyl.

Preferred halo($C_1$-$C_6$)alkoxys and polyhalo($C_1$-$C_6$) alkoxys are halo($C_1$-$C_2$)alkoxys, and polyhalo($C_1$-$C_2$) alkoxys. More preferred are difluoromethoxy and trifluoromethoxy.

Preferred halos are chloro and fluoro.

A preferred trimethylsilyl($C_2$-$C_3$)alkynyl is trimethylsilylethynyl.

$R^{6a}$ and $R^{6b}$ are each independently a hydrogen atom, halo, ($C_1$-$C_8$)alkyl, ($C_2$-$C_6$)alkenyl, ($C_2$-$C_6$)alkynyl, halo ($C_1$-$C_6$)alkyl or polyhalo($C_1$-$C_6$)alkyl, halo($C_2$-$_6$)alkenyl or polyhalo($C_2$-$C_6$)alkenyl, halo($C_2$-$C_6$)alkynyl or polyhalo ($C_2$-$C_6$)alkynyl, ($C_1$-$C_6$)alkoxy($C_1$-$C_4$)alkyl, ($C_1$-$C_6$) alkoxy, ($C_1$-$C_6$)alkylthio, ($C_1$-$C_3$)alkoxycarbonyl, ($C_1$-$C_3$) alkoxycarbonyl($C_1$-$C_3$)alkyl, cyclo($C_3$-$C_7$)alkyl, halo ($C_1$-$C_6$)alkylthio, polyhalo($C_1$-$C_6$)alkythio, halo($C_1$-$C_6$) alkoxy, polyhalo($C_1$-$C_6$)alkoxy, ($C_4$-$C_5$)heterocyclyl, ($C_1$-$C_3$)alkylamino, di($C_1$-$C_3$)alkylamino, di($C_1$-$C_3$) alkylaminocarbonyl, cyano, aryl, aryloxy, ar($C_1$-$C_4$)alkyl, or aryl, aryloxy or ar($C_1$-$C_4$)alkyl substituted on the aryl ring with up to three substituents independently selected from the group consisting of halo, ($C_1$-$C_6$)alkyl, cyclo ($C_5$-$C_6$)alkyl, ($C_2$-$C_6$)alkenyl, cyclo($C_3$-$C_8$)alkenyl, ($C_2$-$C_6$)alkynyl, halo($C_1$-$C_6$)alkyl, polyhalo($C_1$-$C_6$)alkyl, halo($C_2$-$C_6$)alkenyl, polyhalo($C_2$-$C_6$)alkenyl, halo($C_2$-$C_6$) alkynyl, polyhalo($C_2$-$C_6$)alkynyl, ($C_1$-$C_6$)alkoxy, ($C_1$-$C_6$) alkylthio, ($C_1$-$C_6$)alkylsulfonyl, ($C_1$-$C_6$)alkylsulfinyl, phenyl, phen($C_1$-$C_6$)alkyl, phen($C_2$-$C_6$)alkenyl, phen ($C_2$-$C_6$)alkynyl, cyano, halo($C_1$-$C_6$)alkoxy, 1,3-dioxalan-2-yl, hydroxyimino and nitro.

Preferred aryls are phenyl or phenyl independently substituted with up to two substituents independently selected from halo, methyl, ethyl and trifluoromethyl. More preferred are phenyl and monosubstituted phenyl.

Preferred ($C_1$-$C_3$)alkyls are ($C_1$-$C_4$)alkyls. More preferred are methyl, ethyl, n-propyl, isopropyl and n-butyl. Preferred ($C_2$-$C_6$)alkenyls are ($C_2$-$C_4$)alkenyls. More preferred are 2-methyl-1-propenyl and allyl.

Preferred ($C_4$-$C_5$)heterocyclyls are 3-thienyl, 3-furyl, 2-thienyl and 4pyridyl. Most preferred is 3-thienyl.

Preferred ($C_1$-$C_6$)alkoxys are ($C_1$-$C_3$)alkoxys. More preferred are methoxy and ethoxy.

A preferred ($C_1$-$C_3$)alkoxycarbonyl is ethoxycarbonyl.

Preferred ($C_2$-$C_6$)alkynyls are ($C_2$-$C_4$)alkynyls. More preferred are but-2-ynyl, but-3-ynyl and propargyl.

Preferred halos are fluoro, bromo, and chloro. More preferred are chloro and bromo.

Preferred halo($C_1$-$C_6$)alkyls and polyhalo($C_1$-$C_6$)alkyls are halo($C_1$-$C_4$)alkyls and polyhalo($C_1$-$C_3$)alkyls. More preferred are trifluoromethyl, pentafluoroethyl, trichloromethyl, bromomethyl, chloromethyl, difluoromethyl, and chlorodifluoromethyl.

Preferred halo($C_2$-$C_6$)alkenyls or polyhalo($C_2$-$C_6$) alkenyls are halo($C_2$-$C_3$)alkenyls and polyhalo($C_2$-$C_3$) alkenyls.

Preferred halo($C_2$-$C_6$)alkynyls are halo($C_2$-$C_3$)alkynyls.

Preferred halo($C_1$-$C_6$)alkoxys and polyhalo($C_1$-$C_6$) alkoxys are halo($C_1$-$C_3$)alkoxys and polyhalo($C_1$-$C_3$) alkoxys. More preferred are difluoromethoxy and trifluoromethoxy.

Preferred ($C_1$-$C_6$)alkylthios are ($C_1$-$C_3$)alkylthios. More preferred is methylthio.

A preferred ($C_1$-$C_6$)alkoxy($C_1$-$C_4$)alkyl is methoxymethyl.

A preferred ar($C_1$-$C_4$)alkyl is benzyl.

Preferred cyclo($C_3$-$C_7$)alkyls are cyclopropyl, cyclobutyl and cyclopentyl.

A preferred di($C_1$-$C_3$)alkylamino is dimethylamino.

A preferred di($C_1$-$C_3$)alkylaminocarbonyl is dimethylaminocarbonyl. X is an oxygen atom or a sulfur atom.

A preferred X is an oxygen atom.

A second aspect of this invention relates to herbicidal compositions comprising 2-aryl-5,6-dihydropyrimidinone compounds having the general formula

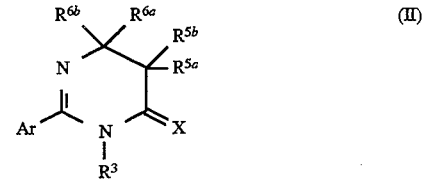

wherein

Ar is a substituted or unsubstituted aryl or heteroaryl;

$R^3$ is an alkyl, haloalkyl, polyhaloalkyl, alkenyl, haloalkenyl, polyhaloalkenyl, alkynyl, haloalkynyl, polyhaloalkynyl, alkenynyl, alkoxyalkyl, dialkoxyalkyl, haloalkoxyalkyl, oxoalkyl, trimethylsilylalkynyl or cyanoalkyl;

$R^{5a}$ and $R^{5b}$ are each independently a hydrogen atom, halo, alkyl, alkenyl, alkynyl, alkoxy, alkylthio, alkoxycarbonyl, alkoxycarbonylalkyl, haloalkyl, haloalkenyl, haloalkynyl, haloalkoxy, polyhaloalkyl, polyhaloalkenyl, polyhaloalkynyl, polyhaloalkoxy, trimethylsilylalkynyl or cyano;

$R^{6a}$ and $R^{6b}$ are each independently a hydrogen atom, halo, alkyl, alkenyl, alkynyl, alkoxy, alkylthio, haloalkylthio, alkoxyalkyl, alkoxycarbonyl, alkoxycarbonylalkyl, haloalkyl, haloalkoxy, haloalkenyl, haloalkynyl, polyhaloalkyl, polyhaloalkoxy, polyhaloalkylthio, polyhaloalkenyl, polyhaloalkynyl, cycloalkyl, aryl, aryloxy, heterocyclyl, aralkyl, alkylamino, dialkylamino, dialkylaminocarbonyl or cyano;

$R^{5a}$ and $R^{6a}$ taken together with the carbon atoms to which they are attached may form a fused 4–7 member ring containing 2–5 methylenes;

X is an oxygen or a sulfur atom; and an agronomically acceptable carrier.

More particularly in this second aspect of this invention comprising compounds having the general formula (II), Ar is furyl, phenyl, naphthyl, pyridyl or thienyl, or furyl, phenyl, naphthyl, pyridyl or thienyl substituted with up to three substituents independently selected from bromo, chloro, fluoro, $(C_1-C_{12})$alkyl, cyclo$(C_3-C_8)$alkyl, $(C_2-C_{12})$ alkenyl, cyclo$(C_3-C_8)$alkenyl, $(C_2-C_{12})$alkynyl, halo $(C_1-C_{12})$alkyl, polyhalo$(C_1-C_{12})$alkyl, halo$(C_2-C_{12})$ alkenyl, polyhalo$(C_2-C_{12})$alkenyl, halo$(C_2-C_6)$alkynyl, polyhalo$(C_2-C_6)$alkynyl, $(C_1-C_{12})$alkoxy, $(C_1-C_{12})$ alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen $(C_2-C_{12})$alkynyl, cyano, halo$(C_1-C_{12})$alkoxy, 1,3-dioxalan-2-yl, hydroxyimino, polyhalo$(C_1-C_{12})$alkoxy and nitro.

Preferred phenyl groups are phenyl, 3-methylphenyl, 3-methoxyphenyl, 3-nitrophenyl, 4-fluorophenyl, 4-chlorophenyl, 3- trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)phenyl, 3(hydroxyimino)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, and 3,4,5-trifluorophenyl. More preferred phenyl groups are phenyl, 3-fluorophenyl, 3,5-difluorophenyl, 3,5-dichlorophenyl and 3-chlorophenyl.

Preferred pyridyl groups are 6-chloro-2-pyridyl; 3-pyridyl; 5-bromo-3-pyridyl, 5,6-dichloro-3-pyridyl, 5-chloro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4-pyridyl and 2,6-dichloro-4-pyridyl. More preferred pyridyl groups are 2-chloro-4-pyridyl, 2-fluoro-4-pyridyl, 5-chloro-3-pyridyl and 2,6-dichloro-4-pyridyl.

Preferred furyl groups are 2-furyl and 3-furyl.

A preferred naphthyl group is 2-naphthyl.

Preferred thienyl groups are 2-thienyl, 3-thienyl, 4-chloro-2-thienyl, 5-chloro-2-thienyl, 5-chloro-3-thienyl and 2,5-dichloro-3-thienyl. A more preferred thienyl group is 5-chloro-3-thienyl.

$R^3$ is $(C_1-C_3)$alkyl, halo$(C_1-C_3)$alkyl, polyhalo$(C_1-C_3)$ alkyl, $(C_3-C_4)$alkenyl, halo$(C_3-C_4)$alkenyl, polyhalo $(C_3-C_4)$alkenyl, $(C_3-C_6)$alkynyl, halo$(C_3-C_6)$alkynyl, polyhalo$(C_3-C_6)$alkynyl, $(C_5-C_6)$alkenynyl, $(C_1-C_6)$alkoxy $(C_1-C_6)$alkyl, di$(C_1-C_6)$alkoxy$(C_1-C_6)$alkyl, halo$(C_1-C_6)$ alkoxy$(C_1-C_6)$alkyl, 2-oxo$(C_2-C_3)$alkyl, trimethylsilyl $(C_3-C_4)$alkynyl or cyano$(C_1-C_6)$alkyl group.

A preferred $(C_1-C_3)$alkyl group is ethyl.

Preferred alkenyl and haloalkenyl groups are $(C_3-C_4)$ alkenyls or halo$(C_3-C_4)$alkenyls. More preferred are allyl and 3-chloroallyl.

Preferred alkynyl groups are $(C_3-C_6)$alkynyl, such as pentynyl, propargyl and 2-butynyl. More preferred alkynyl groups are 2-pentynyl, propargyl, and 2-butynyl.

Preferred halo substituted $(C_3-C_6)$alkynyl groups are halo $(C_3-C_4)$alkynyl. More preferred are iodopropargyl and bromopropargyl.

Preferred $(C_1-C_6)$alkoxy$(C_1-C_6)$alkyls are $(C_1-C_2)$ alkoxy$(C_1-C_3)$alkyl. More preferred are methoxymethyl and 2-methoxyethyl. Most preferred is methoxymethyl.

Preferred di$(C_1-C_6)$alkoxy$(C_1-C_6)$alkyls are di$(C_1-C_2)$ alkoxy$(C_1-C_3)$alkyls. More preferred is 2,2-dimethoxypropyl.

A preferred 2-oxo$(C_2-C_3)$alkyl is acetonyl.

A preferred trimethylsilyl $(C_3-C_4)$alkynyl is 3-(trimethylsilyl)propargyl.

A preferred $(C_5-C_6)$alkenynyl is pent-4-en-2-ynyl.

A preferred cyano $(C_1-C_6)$alkyl is cyanomethyl.

$R^{5a}$ and $R^{5b}$ are each independently a hydrogen atom, $(C_1-C_6)$alkyl, $(C_2-C_6)$alkenyl, $(C_2-C_6)$alkynyl, trimethylsilyl$(C_2-C_3)$alkynyl, $(C_1-C_6)$alkoxy, halo$(C_1-C_6)$ alkyl, polyhalo$(C_1-C_6)$alkyl, halo$(C_2-C_6)$alkenyl, polyhalo $(C_2-C_6)$alkenyl, halo$(C_2-C_6)$alkynyl, polyhalo$(C_2-C_6)$ alkynyl, halo$(C_1-C_6)$alkoxy, polyhalo$(C_1-C_6)$alkoxy, $(C_1-C_6)$alkoxycarbonyl, $(C_1-C_3)$alkoxycarbonyl$(C_1-C_3)$ alkyl, $(C_1-C_6)$alkylthio, halo or cyano.

Preferred $(C_1-C_6)$alkyls are methyl, ethyl, n-propyl and isopropyl. More preferred are methyl and ethyl.

Preferred $(C_2-C_6)$alkynyls are $(C_2-C_3)$alkynyls. More preferred is propargyl.

Preferred $(C_1-C_6)$alkoxys are $(C_1-C_2)$alkoxys. More preferred is methoxy.

Preferred $(C_1-C_6)$alkylthios are $(C_1-C_2)$alkylthios. More preferred is methylthio.

Preferred $(C_1-C_6)$alkoxycarbonyls are $(C_1-C_3)$ alkoxycarbonyls. More preferred are methoxycarbonyl and ethoxycarbonyl.

A preferred $(C_1-C_3)$alkoxycarbonyl$(C_1-C_3)$alkyl is methoxycarbonylmethyl.

Preferred $(C_2-C_6)$alkenyls are $(C_2-C_3)$alkenyls. More preferred is allyl.

Preferred halo$(C_1-C_6)$alkyls and polyhalo$(C_1-C_6)$alkyls are halo$(C_1-C_2)$alkyls and polyhalo$(C_1-C_2)$alkyls. More preferred is fluoromethyl and trifluoromethyl.

Preferred halo$(C_1-C_6)$alkoxys and polyhalo$(C_1-C_6)$ alkoxys are halo$(C_1-C_2)$alkoxys, and polyhalo$(C_1-C_2)$ alkoxys. More preferred are difluoromethoxy and trifluoromethoxy.

Preferred halos are chloro and fluoro.

A preferred trimethylsilyl$(C_2-C_3)$alkynyl is trimethylsilylethynyl.

$R^{6a}$ and $R^{6b}$ are each independently a hydrogen atom, halo, $(C_1-C_8)$alkyl, $(C_2-C_6)$alkenyl, $(C_2-C_6)$alkynyl, halo $(C_1-C_6)$alkyl or polyhalo$(C_1-C_6)$alkyl, halo$(C_2-C_6)$alkenyl or polyhalo$(C_2-C_6)$alkenyl, halo$(C_2-C_6)$alkynyl or polyhalo $(C_2-C_6)$alkynyl, $(C_1-C_6)$alkoxy$(C_1-C_4)$alkyl, $(C_1-C_6)$ alkoxy, $(C_1-C_6)$alkylthio, $(C_1-C_3)$alkoxycarbonyl, $(C_1-C_3)$ alkoxycarbonyl$(C_1-C_3)$alkyl, cyclo$(C_3-C_7)$alkyl, halo $(C_1-C_6)$alkylthio, polyhalo$(C_1-C_6)$alkthio, halo$(C_1-C_6)$ alkoxy, polyhalo$(C_1-C_6)$alkoxy, $(C_4-C_5)$heterocydyl, $(C_1-C_3)$alkylamino, di$(C_1-C_3)$alkylamino, di$(C_1-C_3)$ alkylaminocarbonyl, cyano, aryl, aryloxy, ar$(C_1-C_4)$alkyl, or aryl, aryloxy or ar$(C_1-C_4)$alkyl substituted on the aryl ring with up to three substituents independently selected from the group consisting of halo, $(C_1-C_6)$alkyl, cyclo $(C_5-C_6)$alkyl, $(C_2-C_6)$alkenyl, cyclo$(C_3-C_8)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$ alkynyl, polyhalo$(C_2-C_6)$alkynyl, $(C_1-C_6)$alkoxy, $(C_1-C_6)$ alkylthio, $(C_1-C_6)$alkylsulfonyl, $(C_1-C_6)$alkylsulfinyl, phenyl, phen$(C_1-C_6)$alkyl, phen$(C_2-C_6)$alkenyl, phen $(C_2-C_6)$alkynyl, cyano, halo$(C_1-C_6)$alkoxy, 1,3-dioxalan-2-yl, hydroxyimino and nitro.

Preferred aryls are phenyl or phenyl independently substituted with up to two substituents independently selected from halo, methyl, ethyl and trifluoromethyl. More preferred are phenyl and monosubstituted phenyl.

Preferred $(C_1-C_8)$alkyls are $(C_1-C_4)$alkyls. More preferred are methyl, ethyl, n-propyl, isopropyl and n-butyl.

Preferred $(C_2-C_6)$alkenyls are $(C_2-C_4)$alkenyls. More preferred are 2-methyl-1-propenyl and allyl.

Preferred $(C_4-C_5)$heterocyclyls are 3-thienyl, 3-furyl, 2-thienyl and 4pyridyl. Most preferred is 3-thienyl.

Preferred $(C_1-C_6)$alkoxys are $(C_1-C_3)$alkoxys. More preferred are methoxy and ethoxy.

A preferred $(C_1-C_3)$alkoxycarbonyl is ethoxycarbonyl.

Preferred $(C_2-C_6)$alkynyls are $(C_2-C_4)$alkynyls. More preferred are but2-ynyl, but-3-ynyl and propargyl.

Preferred halos are fluoro, bromo, and chloro. More preferred are chloro and bromo.

Preferred halo($C_1$–$C_6$)alkyls and polyhalo($C_1$–$C_6$)alkyls are halo($C_1$–$C_4$)alkyls and polyhalo($C_1$–$C_3$)alkyls. More preferred are trifluoromethyl, pentafluoroethyl, trichloromethyl, bromomethyl, chloromethyl, difluoromethyl, and chlorodifluoromethyl.

Preferred halo($C_2$–$C_6$)alkenyls or polyhalo($C_2$–$C_6$) alkenyls are halo($C_2$–$C_3$)alkenyls and polyhalo($C_2$–$C_3$) alkenyls.

Preferred halo($C_2$–$C_6$)alkynyls are halo($C_2$–$C_3$)alkynyls.

Preferred halo($C_1$–$C_6$)alkoxys and polyhalo($C_1$–$C_6$) alkoxys are halo($C_1$–$C_3$)alkoxys and polyhalo($C_1$–$C_3$) alkoxys. More preferred are difluoromethoxy and trifluoromethoxy.

Preferred ($C_1$–$C_6$)alkylthios are ($C_1$–$C_3$)alkylthios. More preferred is methylthio.

A preferred ($C_1$–$C_6$)alkoxy($C_1$–$C_4$)alkyl is methoxymethyl.

A preferred ar($C_1$–$C_4$)alkyl is benzyl.

Preferred cyclo($C_3$–$C_7$)alkyls are cyclopropyl, cyclobutyl and cyclopentyl.

A preferred di($C_1$–$C_3$)alkylamino is dimethylamino.

A preferred di($C_1$–$C_3$)alkylaminocarbonyl is dimethylaminocarbonyl. X is an oxygen atom or a sulfur atom.

A preferred X is an oxygen atom.

A third aspect of this invention relates to a method of controlling a weed comprising applying a herbicidally effective amount of a composition comprising 2-aryl-5,6-dihydropyrimidinone compounds having the general formula (11) and an agronomically acceptable carrier to the weed, to the locus of the weed or to the growth medium of said weed.

The following general experimental procedures were employed to synthesize representative 2-aryl-5,6-dihydropyrimidinone compounds of this invention.

METHOD A

An amidine 1 is reacted with an acrolein derivative 2 in a ketone, ether, aromatic hydrocarbon, chlorocarbon or amide solvent at −70° C. to 100° C. to give a 4-hydroxy-3,4,5,6-tetrahydropyrimidine 3. This is oxidized with for example $KMnO_4$ in a ketone solvent at −40° C. to 50° C. to afford a 5,6-dihydropyrimidin-4-one 4 which is alkylated with $R^3X$, wherein X=halo, alkanesulfonate, arenesulfonate or haloalkanesulfonate, in a nitrile, amide or ethereal solvent using an alkyllithium, an alkali metal hydride or an alkali metal alkoxide as base to give a compound of the invention wherein $R^{5b}$ is a hydrogen atom.

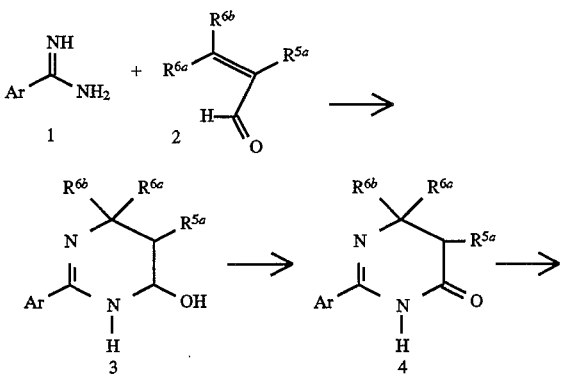

-continued

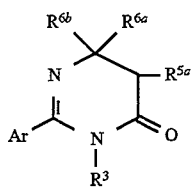

METHOD B1

An amidine 1 is reacted with an enedioate in a ketone or amide solvent at 0° C. to 100° C. to give a 5-carboalkoxy-5,6-dihydropyrimidinone 5. A substituent $R^{5a}$ can be introduced at the 5-position to give 6 by alkylation with $R^{5a}X$, wherein X=halo, alkanesulfonate, arenesulfonate or haloalkanesulfonate in acetonitrile or an amide as solvent with either sodium hydride or alkoxide as base at 0° C. to 100° C. This is followed by alkylation on nitrogen with $R^3X$, wherein X=halo, alkanesulfonate, arenesulfonate or haloalkanesulfonate, in acetonitrile or an amide as solvent, sodium hydride or an alkoxide as base at 0° C. to 100° C., to afford compounds of the invention in which $R^{5b}$=($C_1$–$C_6$) alkoxycarbonyl. Deesterification and decarboxylation gives compounds of the invention in which $R^{5b}$=a hydrogen atom.

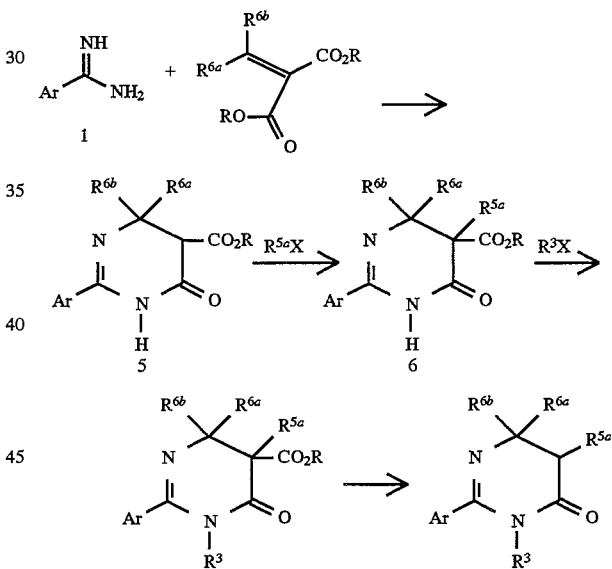

METHOD B2

An N-substituted amidine 1a, or its salt, is reacted with an enedioate in a ketone or amide solvent at 0° C. to 100° C. to give a compound of the invention. When the amidine salt is used, a base is added such as an alkali metal bicarbonate or carbonate.

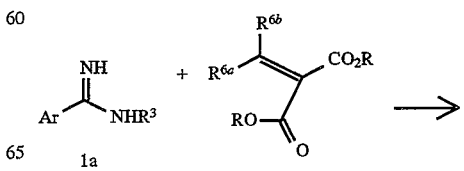

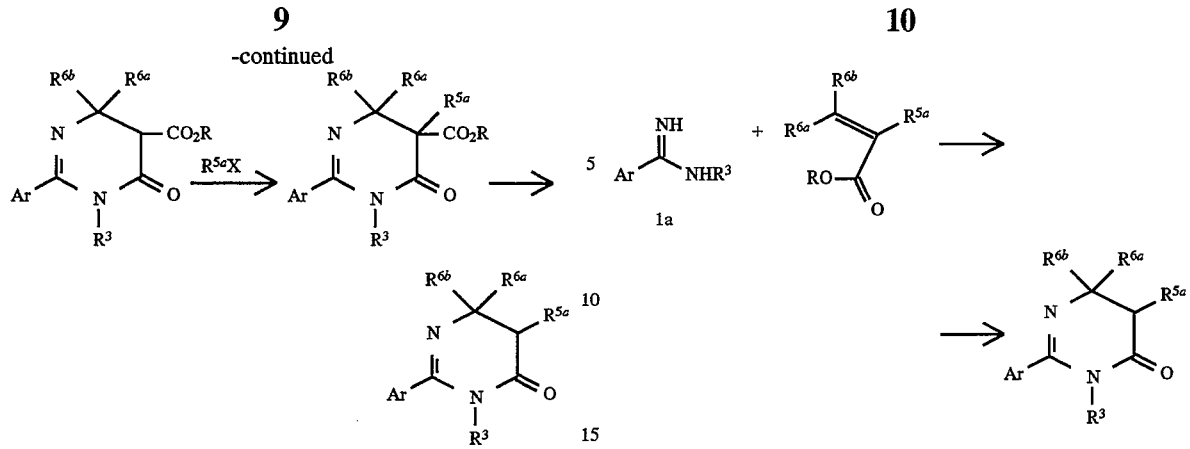

METHOD C1

An amidine 1, or its salt, is reacted with an enoate in a ketone, ether, amide or nitrile solvent at 0° C. to 100° C. to give a dihydropyrimidin-4-one 4 which is alkylated with $R^3X$, wherein X=halo, alkanesulfonate, arenesulfonate or haloalkanesulfonate, in a nitrile, amide or ethereal solvent using an alkyllithium, an alkali metal hydride or an alkali metal alkoxide as base to give a compound of the invention. When the amidine salt is used a base is added, for example an alkali metal bicarbonate or carbonate, a tertiary amine or pyridine.

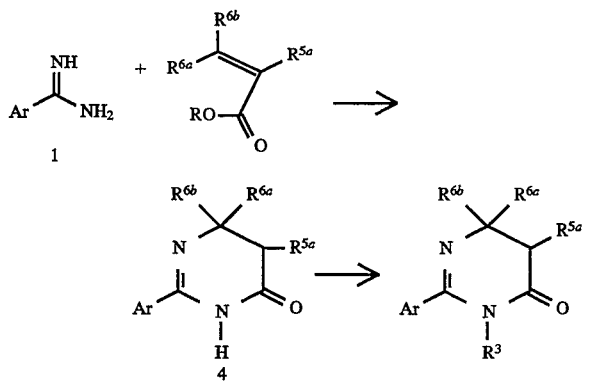

METHOD C2

An N-substituted amidine 1a, or its salt, is reacted with an enoate in an ether, ketone, amide or nitrile solvent at 0° C. to 100° C. to give a compound of the invention. When the amidine salt is used a base is added, for example an alkali metal bicarbonate or carbonate, a tertiary amine or pyridine. The amidine salt may be prepared and used in-situ.

METHOD D

An amidine 1 is reacted with an α,β-unsaturated acid chloride in an aromatic or ethereal solvent such as toluene or diglyme at 100°–200° C. in the presence of an amine base such as pyridine to give a dihydropyrimidin-4-one 4 which is alkylated with $R^3X$, wherein X=halo, alkanesulfonate, arenesulfonate or haloalkanesulfonate, in a nitrile, amide or ethereal solvent using an alkyllithium, an alkali metal hydride or an alkali metal alkoxide as base to give a compound of the invention.

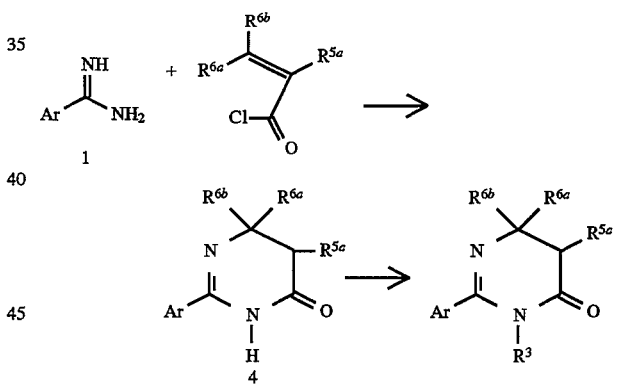

Table I lists representative compounds synthesized and used in the present invention. These compounds are provided merely to illustrate their methods of preparation and their use in the method of the present invention. They are not intended to limit the scope of the invention which is defined by the claims.

TABLE I

Structures of Prepared Compounds

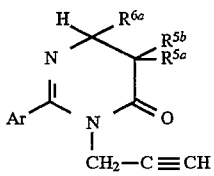

$$\text{CH}_2-\text{C}\equiv\text{CH}$$

| Cmpd. No. | Synthesis Method* | Ar | $R^{5a}$ | $R^{5b}$ | $R^{6a}$ |
|---|---|---|---|---|---|
| 1 | A | phenyl | $CH_3$ | H | $C_2H_5$ |
| 2 | B2 | phenyl | $CO_2C_2H_5$ | H | $CF_3$ |
| 3 | B1 | phenyl | $CO_2C_2H_5$ | $CH_2C\equiv CH$ | $CF_3$ |
| 4 | B1 | phenyl | $CO_2C_2H_5$ | $C_2H_5$ | $CF_3$ |
| 5 | B1 | phenyl | $CO_2CH_3$ | $C_2H_5$ | $CF_3$ |
| 6 | B1 | phenyl | $C_2H_5$ | H | $CF_3$ |
| 7 | B1 | 2,6-dichloro-4-pyridyl | $CO_2CH_3$ | $C_2H_5$ | $C_2H_5$ |
| 8 | B1 | 2,6-dichloro-4-pyridyl | $C_2H_5$ | H | $C_2H_5$ |
| 9 | B2 | 2,6-dichloro-4-pyridyl | $CO_2CH_3$ | H | $C_2H_5$ |
| 10 | C2 | phenyl | H | H | $CF_3$ |
| 11 | C1 | phenyl | H | H | $CH_3$ |
| 12 | B2 | 2,6-dichloro-4-pyridyl | H | H | $C_2H_5$ |
| 13 | C1 | 3,5-dichlorophenyl | H | H | $CF_3$ |
| 14 | C1 | 3-chlorophenyl | H | H | $CF_3$ |
| 15 | D | phenyl | H | H | phenyl |

*SYNTHESIS METHODS:
A = aldehyde + amidine
B1 = enedioate + amidine
B2 = enedioate + N-propargylamidine
C1 = enoate + amidine
C2 = enoate + N-propargylamidine
D = enoyl chloride + amidine

EXAMPLE 1

Preparation of 6-ethyl-5-methyl-2-phenyl-3-propargyl-5,6-dihydropyrimidin-4-one (Compound 1)

Step 1: Preparation of 6-ethyl-5-methyl-4-hydroxy-2-phenyl-3,4,5,6-tetrahydropyrimidine To an ice cooled mixture of 19.98 g (16.6 mmol) of benzamidine in 80 mL of acetone, was added dropwise over two hours, a solution of 16.35g (16.6 mmol) 2-methyl-2-pentenal and 0.055 g 1,4-hydroquinone, in acetone. The mixture was left to stir cold and warm to room temperature over 20 hours. The product was isolated by vacuum filtration and was washed with a minimal amount of acetone. 15.6 g (44%) of 6-ethyl-5-methyl-4-hydroxy-2-phenyl-3,4,5,6-tetrahydropyrimidine was collected, as a white solid.

$^1$H-NMR ($d_6$-DMSO) 0.95(3H,m), 1.38(2H,m),1.7(1H,m), 3.05(1H,m), 3.35(1H,bs), 4.55–4.7(1H,m), 5.3(1H,bs), 7.35(3H,m), 7.8(2H,m).

Step 2: Preparation of 6-ethyl-5-methyl-2-phenyl-5,6-dihydropyrimidin-4-one

A mixture of 6.58 g (30.6 mmol) of 6-ethyl-5-methyl-4-hydroxy-2-phenyl-3,4,5,6-tetrahydropyrimidine and 300 mL of acetone was warmed to 35° C. for 1 hour to help dissolve the tetrahydropyrimidine. A cloudy solution resulted. The solution was cooled to 10° C. and 14.0 g (25.3 mmol) of potassium permanganate was added, in batches. The mixture was stirred at room temperature for 20 hours then 50 mL of absolute ethanol was added and the reaction mixture was stirred for an additional 1.25 hours. The reaction mixture was gravity filtered and the filtrate was concentrated. Ether was added to the residue and the solution was filtered again. Concentration of the filtrate left 6.0 g of a sticky white solid behind. The crude product was purified by passing through a 4 inch plug of silica gel washing with 500 mL of 40% tetrahydrofuran/60% hexane. The eluate was concentrated to yield 3.98 g (62%) 6-ethyl-5-methyl-2-phenyl-5,6-dihydropyrimidin-4-one, as a white solid.

$^1$H-NMR (CDCl$_3$) d 1.1(3H,t), 1.28(3H,d), 1.65(1H,m), 1.81(1H,m), 2.4(1H,m), 3.44(1H,m), 7.48(3H,m), 7.8(2H, d).

Step 3: Preparation of 6-ethyl-5-methyl-2-phenyl-3-propargyl-5,6-dihydropyrimidin-4-one Oven dried glassware and a nitrogen purge were utilized. 3.22 mL of 1.6 Molar n-butyl lithium in hexanes (5.15 mmol) was added dropwise to a solution of 1.06 g (4.93 mmol) of 6-ethyl-5-methyl-2-phenyl-5,6-dihydropyrimidin-4-one, in 15 mL of dry tetrahydrofuran, at −50 to −60° C. The mixture was stirred for 15 minutes and then 0.8 mL (5.38 mmol) of 80 wt.% propargyl bromide in toluene was added at −65° C. The ice bath was removed after 1.5 hours and the reaction mixture was stirred for an additional 20 hours. The solvent had evaporated overnight. Ether was added and the reaction mixture was washed three times with water followed by three times with 3 Molar hydrochloric acid. The acidic aqueous washes were combined, cooled externally, and 50% sodium hydroxide was added until the pH=10, then extracted three times with ether. The ether extracts were combined, dried over magnesium sulfate, and concentrated to yield 0.68 g of crude product. The crude product was combined with crude product obtained from previous reactions and purified on a six inch plug of basic alumina by washing with 400 mL of methylene chloride. The filtrate was concentrated to yield 6-ethyl-5-methyl-2-phenyl-3-propargyl-5,6-dihydropyrimidin-4-one (Compound 1), as a yellow solid, melting 62°–65° C.

$^1$H-NMR (CDCl$_3$) d 1.1(3H,t), 1.18(3H,d), 1.7(2H,m), 2.2(1H,t), 2.48(1H,m), 3.35(1H,m), 4.3(2H,d), 7.5(3H,m), 5.6(2H,m).

EXAMPLE 2

Formation of 2-(2,6-dichloro-4-pyridyl)-5,6-diethyl-3-propargyl-5,6-dihydropyrimidine-4-one (Compound 8)

Step 1: Preparation of Methyl 2-methoxycarbonyl-2-pentenoate

To 9.3g (160 mmol) of propionaldehyde and 10.57 g (80 mmol) of dimethylmalonate was added 50 mL of acetic anhydride and refluxed for 72 hrs. The reaction was cooled to room temperature and the solvent evaporated in vacuo until a constant weight was obtained. The resultant clear liquid that represented 80% pure desired product was used without further purification.

$^1$H NMR (200 MHz, CDCl$_3$) 1.2 (t, 3H), 2.4 (q, 2H), 4.75 (s, 3H), 4.8 (s, 3H), 7.1 (t, 1H).

Step 2: Formation of 2-(2,6-dichloro-4-pyridyl)-6-ethyl-5-methoxycarbonyl-5,6-dihydropyrimidine-4-one To 10.6 g (46.8 mmol) of 2,6-dichloropyridine-4-carboxamidine hydrochloride in 100 mL of dimethylformamide was added 4.62 g of sodium bicarbonate followed by 10 g (46.8 mmol) of 80% methyl 2-methyl-2-pentenoate. The reaction was stirred at room temperature overnight before pouring onto 300 mL of ice water. The resultant pale yellow precipitate was collected by vacuum filtration and yields 12.15 g (36.8 mmol, 79%) of desired product with mp=188°–189° C.

$^1$H NMR (200 MHz, d6-acetone) d 1.1 (t, 3H), 1.8 (m, 2H), 3.5 (d, 1H), 3.8 (s, 3H), 4.0 (m, 1H), 8.0 (s, 2H), 10.2 (s, b, 1H).

Step 3: Formation of 2-(2,6-dichloro-4-pyridyl)-5,6-diethyl-5-methoxycarbonyl-5,6-dihydropyrimidin-4-one To 27.0 g (81.8 mmol) of 2-(2,6-dichloro-4-pyridyl)-6-ethyl-5-methoxycarbonyl5,6-dihydropyrimidin-4-one in 500 mL of dimethylformamide was added at 0° C. over 30 min via a solid addition funnel 19.3 g (172 mmol) of potassium-t-butoxide followed by the dropwise addition over 15 min of 13.3 g (85.2 mmol) of iodoethane. The reaction was stirred at 0° C. for one hour before quenching onto 700 mL of ice water. The aqueous was acidified to pH=1 (conc. HCl) and extracted with EtOAc (3×400 mL). The organics were combined before washing with water (2×500 mL), and saturated NaCl (1×300 mL) drying over MgSO$_4$, filtering and evaporating to dryness in vacuo to give 27.32 g (76.3 mmol, 93%) of the desired product as a pale yellow solid with mp=202°–203° C.

$^1$H NMR (200 MHz,d$_6$-acetone) d 1.0 (t, 3H), 1.2 (t, 3H), 1.6 (m, 1H), 1.8 (m, 1H), 2.1 (m, 1H), 2.4 (m, 1H), 3.6 (s, 3H), 3.65 (t, 1H), 8.0 (s, 2H), 10.3 (s, b, 1H).

Step 4: Formation of 2-(2,6-dichloro-4-pyridyl)-5,6-diethyl-5-methoxycarbonyl-3-propargyl-5,6-dihydropyrimidin-4-one To 3.15 g (78 mmol) of sodium hydride in 50 mL of dimethylformamide at 0° C. was added dropwise over 1.5 hr a solution of 26.9 g (75 mmol) of 2-(2,6-dichloro-4-pyridyl)-5,6-diethyl-5-methoxycarbonyl-5,6-dihydropyrimidin-4-one in 200 mL of dimethylformamide. When this addition was complete 12.5 mL (16.73 g, 112.5 mmol) of 80% propargyl brmide in toluene was added and the reaction stirred at room temperature overnight. Upon completion the reaction was quenched onto 600 mL of ice/water, extracted with ethyl acetate (3×400 mL), the organics were combined, washed with water (2×300 mL) and saturated sodium chloride (2×500 mL), dried over Na$_2$SO$_4$, filtered and evaporated to dryness in vacuo to give 29.23 g (73.8 mmol, 98%) of the desired product as a yellow solid.

$^1$H NMR (200 MHz, d$_6$-acetone) d 1.0 (t, 3H), 1.2 (t, 3H), 1.6 (m, 1H), 1.8 (m, 1H), 2.0 (m, 1H), 2.2 (m, 1H), 2.9 (t, 1H), 3.6 (dd, 1H), 3.7 (s, 3H), 4.4 (d, 2H), 7.7 (s, 2H).

Step 5: Formation of 2-(2,6-dichloro-4-pyridyl)-5,6-diethyl-3-propargyl-5,6-dihydropyrimidin-4-one To 5.0 g (12.6 mmol) of 2-(2,6-dichloro-4-pyridyl)-5,6-diethyl-5-methoxycarbonyl-3-propargyl-5,6-dihydropyrimidin-4-one in 50 mL of pyridine was added 11.5 g (76 mmol) of lithium iodide and refluxed overnight. The reaction was cooled to room temperature, quenched onto 250 mL of water andextracted with EtOAc (2×300 mL). The organics were combined, washed with water (1×200 mL), dilute HCl (2×200 mL), water (1×200 mL), dilute sodium bisulfite (1×200 mL) and saturated sodium chloride (1×200 mL). The EtOAc was diluted with 600 mL of hexanes and vacuum filtered through a pad of silica gel. The filtrate was dried over sodium sulfate, filtered and evaporated to dryness in vacuo. The residue was triturated with diethyl ether and solid impurities removed by filtration. The filtrate was once again evaporated to dryness in vacuo to give 2.2 g (5.75 mmol, 46%) of desired product as an oil.

$^1$H NMR (200 MHz, CDCl$_3$) d 1.0 (m, 6H), 1.6 (m, 4H), 2.1 (t, 1H), 2.5 (m, 1H), 4.8 (m, 1H), 4.1–4.3 (m, 2H), 7.5 (ds, 2H).

EXAMPLE 3

Preparation of 2-(2,6-dichloro-4-pyridyl)-6-ethyl-5-methoxycarbonyl-3-propargyl-5,6-dihydropyrimidin-4-one (Compound 9)

To 1.72 g (10 mmol) of methyl 2-methoxycarbonyl-2-pentenoate in 50 mL of dimethylformamide was added 2.28 g (10 mmol) of 2,6-dichloropyridine-4-(N-propargyl) carboxamidine hydrochloride and 840 mg (10 mmol) of sodium bicarbonate. The reaction was stirred at room temperature overnight, quenched onto 300 mL of water and extracted with EtOAc (3×150 mL). The organics were combined, washed with water (2×300 mL), dried over magnesium sulfate, filtered, and evaporated to dryness in vacuo to give a dark oil. This crude residue was purified by medium pressure liquid chromotography on silica gel with 3:1 hexanes/EtOAc. The desired product is further purified by trituration with hexanes. Unwanted solids are discarded and the filtrate is evaporated to dryness in vacuo to give 500 mg (1.36 mmol, 14%) of product as a clear oil.

$^1$H NMR (200 MHz, CDCl$_3$) d 1.2 (t, 3H), 1.7 (q, 2H), 2.4 (t, 1H), 3.5 (d, 1H), 3.7 (m, 1H), 3.8 (ds, 3H), 4.1–4.5 (m, 2H), 7.5 (ds, 2H).

EXAMPLE 4

Preparation of 2-(3-chlorophenyl)-4-propargyl-6-trifluoromethyl-5,6-dihydropyrimidin-4-one (Compound 14)

Step 1: Preparation of 2-(3-chlorophenyl)-6-trifluoromethyl-5,6-dihydropyrimidin-4-one A mixture of 1.12 g (17.0 mmol) of 3-chlorobenzamidine hydrochloride, 1.4 g (17 mmol) of sodium bicarbonate, 2.55 mL (17 mmol) of ethyl-4,4,4-trifluoromethylcrotonate and 3 mL of dimethylformamide were stirred for 16 hours. The mixture was poured onto crushed ice then vacuum filtered to yield 1.25 g (27%) of 2-(3-chlorophenyl)-6-trifluoromethyl-5,6-dihydropyrimidin-4-one, as a white solid.

$^1$H-NMR (d$_6$-DMSO) d 2.55(2H,m), 4.7(1H,m), 7.6(2H,m), 7.92(2H,m).

Step 2: Preparation of 2-(3-chlorophenyl)-4-propargyl-6-trifluoromethyl-5,6-dihydropyrimidin-4-one To a mixture of 1.23 g (4.45 mmol) of 2-(3-chlorophenyl)-6-trifluoromethyl-5,6-dihydropyrimidin-4-one and 2.5 mL of dimethylformamide, was added 0.5 g (4.45 mmol) of potassium-t-butoxide followed by 0.66 mL (4.45 mmol) of 80 wt.% propargyl bromide in toluene. The reaction mixture was stirred at room temperature for 16 hours, then was poured onto crushed ice. The reaction mixture was transferred to a separatory funnel and extracted two times with ether. The ether layers were combined, dried over magnesium sulfate and concentrated. The crude product was purified on a 40 g silica gel column using 15% ethyl acetate/85% hexane, to yield 0.7 g (50.0%) 2-(3-chlorophenyl)-4-propargyl-6-trifluoromethyl-5,6-dihydropyrimidin-4-one (Compound 14), as a yellow oil.

$^1$H-NMR (CDCl$_3$) d 2.3(1H,t), 2.85(2H,m), 4.25(3H,m), 7.51(4H,m).

EXAMPLE 5

Preparation of 2-phenyl-3-propargyl-6-trifluoromethyl-5,6-dihydropyrimidin-4-one (Compound 10)

A mixture of 2.48 g (13.4 mmol), ethylbenzimidate hydrochloride, 1.12 g (13.4 mmol) of sodium bicarbonate and 10 mL of acetonitrile, were stirred at room temperature for 15 minutes. The reaction mixture was warmed to 50° C., on an oil bath and 0.91 mL (13.4 mmol) of propargylamine was added. After stirring for 0.5 hours, 2.0 mL (13.4 mmol) of ethyl-4,4,4-trifluorocrotonate was added and the reaction was stirred for 16 hours. The reaction was cooled to room temperature and the solvent was removed. Ether was added to the residue and washed 3 times with water followed by 3 times with 3 Molar hydrochloric acid. The organic layer was dried over magnesium sulfate and concentrated to yield 0.44 g (12%) of 2-phenyl-3-propargyl-6-trifluoromethyl-5,6-dihydropyrimidin-4-one (Compound 10), as an oil.

$^1$H-NMR (CDCl$_3$) d 2.25(1H,t), 2.75(1H,dd), 2.93(1H,dd), 4.3(3H,m), 7.01(3H,m), 7.65(2H,m).

EXAMPLE 6

Preparation of 5,6-dihydro-2,6-diphenyl-3-propargylpyrimidin-4-one (Compound 15)

Step 1: Preparation of 5,6-dihydro-2,6-diphenylpyrimidin-4-one

To a stirred suspension of 8.42 g (70.2 mmol) of benzamidine and 8 mL (99.2 mmol) of pyridine in 150 mL of toluene was added dropwise over 10 min a solution of 7.68 g (46.1 mmol) of cinnamoyl chloride in 20 mL of toluene. The mixture was stirred for 10 min at room temperature and heated at reflux for 2 days. The mixture was cooled, diluted with 150 mL of ethyl acetate and extracted with two 125 mL portions of 5% aqueous HCl. The combined aqueous HCl extracts were neutralized by careful addition of 50% aqueous NaOH and extracted with two 250 mL portions of ethyl acetate. These ethyl acetate extracts were combined, dried over MgSO$_4$ and rotovaped to afford 7.80 g of 5,6-dihydro-2,6-diphenylpyrimidin-4-one as a white solid.

$^1$H-NMR (CDCl$_3$) d 2.6 (1H,dd), 2.85 (1H,dd), 4.95 (1H,dd), 7.1–8.0 (10H).

Step 2: Preparation of 5,6-dihydro-2,6-diphenyl-3-propargylpyrimidin-4-one

To a stirred solution of 3.95 g (15.8 mmol) of 5,6-dihydro-2,6-diphenylpyrimidin-4-one in 15 mL of DMF was added 2.07 g (18.5 mmol) of solid potassium t-butoxide. The mixture was stirred for 10 rain and 2.60 g (17.5 mmol) of an 80% by weight solution of propargyl bromide in toluene was added. The mixture was stirred at room temperature for 4 days, diluted with 175 mL of ether, washed with four 50 mL portions of water and dried over MgSO$_4$. Removal of the solvent on the rotovap left 2.47 g of crude product which was purified by flash chromatography on silica gel eluted with an ether-hexane gradient to afford 0.72 g of 5,6-dihydro-2,6-diphenyl-3-propargylpyrimidin-4-one (Compound 15) as an oil.

$^1$H-NMR (CDCl$_3$) d 2.2 (1H,t), 2.75 (1H,dd), 2.95 (1H,dd), 4.25 (1H,dd), 4.40 (1H,dd), 4.9 (1H,dd), 7.2–7.8 (10H).

By analogous methods, as listed in Table I, compounds 2–7 and 11–13 were also prepared. The $^1$H-NMR data for these compounds are presented in Table II. These compounds were oils except for compound 11 which melted at 74.5°–77° C.

TABLE II

| Cmpd. No. | NMR of Compounds 2–7 & 11–13 |
|---|---|
| 2 | $^1$H NMR(200MHz, CDCl$_3$)d 1.3(t, 3H), 2.3(t, 1H), 3.9(d, 1H), 4.4(m, 4H), 4.8(m, 1H), 7.5(m, 3H), 7.6(m, 2H). |
| 3 | $^1$H NMR(200MHz, CDCl$_3$)d 1.3(t, 3H)2.1(s, 1H), 2.3(s, 1H), 3.2(d, 1H), 3.6(d, 1H), 4.2(m, 2H), 4.3(s, 1H), 5.0(q, 1H), 7.5(m, 3H), 7.6(m, 2H). |
| 4 | $^1$H NMR(200MHz, CDCl$_3$)d 1.0(t, 3H), 1.3(t, 3H), 2.2(t, 1H), 2.3(m, 1H), 2.6(m, 1H), 4.2(q, 2H), 4.3–4.5(m, 3H), 7.5(m, 3H), 7.6(m, 2H). |

TABLE II-continued

NMR of Compounds 2-7 & 11-13

| Cmpd. No. | |
|---|---|
| 5 | $^1$H NMR(200MHz, CDCl$_3$)d 1.0(t, 3H), 2.2(t, 1H), 2.3(m, 1H), 2.6(m, 1H), 3.7(s, 3H), 4.2–4.6(m, 3H), 7.5(m, 3H), 7.6(m, 2H). |
| 6 | $^1$H NMR(200MHz, CDCl$_3$)d 1.0(t, 3H), 1.9(m, 2H), 2.3(t, 1H), 2.9(m, 1H), 4.3(m, 3H), 7.5(m, 3H), 7.6(m, 2H). |
| 7 | $^1$H NMR(200MHZ, CDCl$_3$)d 1.0(t, 3H), 1.2(t, 3H), 1.8(m, 2H), 2.0(m, 1H), 2.4(t, 1H), 2.45(m, 1H), 3.5(dd, 1H), 3.7(s, 3H), 4.2(dd, 1H), 4.4(dd, 1H), 7.5(s, 2H). |
| 11 | $^1$H NMR(200MHZ, CDCl$_3$) 1.4(3H, d), 2.2(1H, t), 2.42(1H, dd), 2.7(1H, dd), 3.9(1H, m), 4.3(2H, d), 7.48(3H, m), 7.64(2H, m) |
| 12 | $^1$H NMR(200MHZ, CDCl$_3$) 1.1(3H, t), 1.75(2H, m), 2.35(1H, t), 2.45(1H, dd), 2.7(1H, dd), 3.69(1, H, m), 4.2(2H, d), 7.55(2H, s) |
| 13 | $^1$H NMR(200MHZ, CDCl$_3$) 2.33(1H, t), 2.73(1H, dd), 2.92(1H, dd), 4.25(3H, m), 7.65(3H, m) |

Table III lists representative compounds contemplated by the present invention. They are not intended to limit the scope of the invention which is defined by the claims.

TABLE III

Representative Compounds Contemplated by the Present Invention

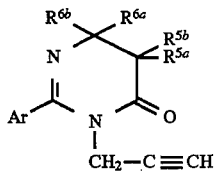

| Cmpd. No. | Ar | R$^{5a}$ | R$^{5b}$ | R$^{6a}$ | R$^{6b}$ |
|---|---|---|---|---|---|
| 16 | 5-chloro-3-pyridyl | H | H | CF$_3$ | H |
| 17 | phenyl | H | H | CF$_3$ | CF$_3$ |
| 18 | phenyl | H | H | CF$_3$ | CH$_3$ |
| 19 | phenyl | CH$_3$ | H | CF$_3$ | H |
| 20 | phenyl | CH$_3$ | CH$_3$ | H | H |
| 21 | 3-chlorophenyl | H | H | C$_2$H$_5$ | H |
| 22 | 2,6-dichloro-4-pyridyl | H | H | CH(CH$_3$)$_2$ | H |
| 23 | 2-chloro-4-pyridyl | H | H | CH$_3$ | H |
| 24 | 3-fluorophenyl | H | H | CF$_3$ | H |
| 25 | 3-methoxyphenyl | H | H | CF$_3$ | H |
| 26 | 3-methylphenyl | H | H | CF$_3$ | H |
| 27 | 3-trifluoromethylphenyl | H | H | CF$_3$ | H |
| 28 | 3-chlorophenyl | CH$_3$ | H | CF$_3$ | H |
| 29 | 3-chlorophenyl | C$_2$H$_5$ | H | CF$_3$ | H |
| 30 | 3-chlorophenyl | C$_2$H$_5$ | H | CCl$_3$ | H |
| 31 | 2-chlorophenyl | H | H | CF$_3$ | H |
| 32 | 4-chlorophenyl | H | H | CF$_3$ | H |

The 2-aryl-5,6-dihydropyrimidinone compounds of this invention are useful as preemergence and postemergence herbicides. In general, they require lower doses to control weeds preemergence. Preemergence herbicides are usually applied to the soil either before, during or after seeding, but before the crop emerges. Postemergence herbicides are applied after the plants have emerged and during their growth period. The embodied materials generally show selectivity to several agronomically important crops such as corn, cotton, rice, soybean, sugarbeet, sunflower, peanut and wheat.

Under some conditions the compounds of the invention may be incorporated into the soil or other growth medium prior to planting a crop. This incorporation may be by any convenient means, including mixing with the soil, applying the compound to the surface of the soil and then dishing or dragging into the soil to the desired depth, or by employing a liquid carrier.

The 2-aryl-5,6-dihydropyrimidinones of the present invention can be applied to various loci such the soil or the foliage. For such purposes these compounds can be used in the technical or pure form as prepared, as solutions or as formulations. The compounds are usually taken up in a carrier or are formulated so as to render them suitable for subsequent dissemination as herbicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual." Allured Publishing Company, Ridgewood, N.J., U.S.A.

The 2-aryl-5,6-dihydropyrimidinones can be applied as herbicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and weeds to be controlled, but the preferred effective amount is usually from about 0.01 lb. to about 10 lbs. per acre of the active ingredient.

As a soil treatment the chemical can be incorporated in the soil or applied to the surface usually at a rate of from about 0.01 to about 10 lbs. per acre. As a foliar spray, the toxicant is usually applied to growing plants at a rate of from about 0.01 to about 10 lbs. per acre. The 2-aryl-5,6-dihydropyrimidinones of the invention can also be mixed with fertilizers or fertilizing materials before their application. In one type of solid fertilizing composition in which the 2-aryl-5,6-dihydropyrimidinones can be used, particles of a fertilizer or fertilizing ingredients, such as ammonium sulfate, ammonium nitrate, or ammonium phosphate, can be coated with one or more of the compounds. The solid compounds and solid fertilizing material can also be admixed in mixing or blending equipment, or they can be incorporated with fertilizers in granular formulations. Any relative proportion of fertilizer can be used which is suitable for the crops and weeds to be treated. The 2-aryl-5,6-dihydropyrimidinone will commonly be from about 5% to about 25% of the fertilizing composition. These compositions provide fertilizing materials which promote the rapid growth of desired plants, and at the same time control the growth of undesired plants.

For some applications, one or more other herbicides may be added of the herbicides of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

CARBOXYLIC ACIDS AND DERIVATIVES 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;
2,3,6-trichlorophenylacetic acid and its salts;
3,6-endoxohexahydrophthalic acid and its salts;
dimethyl 2,3,5,6-tetrachloroterephthalate; trichloroacetic acid and its salts;
2,2-dichloropropionic acid and its salts;
2,3-dichloroisobutyric acid and its salts;
isopropylammonium 2-(4-isopropyl-4-methyl-5-oxo-2-imidazolin-2-yl)nicotinate;
2-[4,5-dihydro-4-methyl-4-(1-methylethyl)-5-oxo-1H-imidazol-2-yl]-3-quinolinecarboxylic acid;
6-(4-isopropyl-4-methyl-5-oxo-2-imidazolin-2-yl)-m-toluic acid, methyl ester and
6-(4-isopropyl-4-methyl-5-oxo-2-imidazolin-2-yl)-p-toluic acid, methyl ester;
N-(phosphomethyl)glycine isopropylammonium salt;
[3,5,6-trichloro-(2-pyridinyl)oxy]acetic acid;
3,7-dichloro-8-quinolinecarboxylic acid;
ammonium DL-homoalanin-4-yl(methyl)phosphinate;

CARBAMIC ACID DERIVATIVES ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;
isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts
S-(4-chlorobenzyl)-N,N-diethylthiolcarbamate;

SUBSTITUTED UREAS 2-chloro-N-[(4-methoxy-6-methyl-1,3,5-triazin-2yl) aminocarbonyl]-benzenesulfonamide;
3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-2-n-butyl-1-methylurea;
3-(3,4-dichlorophenyl)-1-methoxy-1 -methylurea;
3-(4-chlorophenyl)-I -methoxy-I-methylurea;
3-(3,4-dichlorophenyl)-1,1,3-trimethylurea;
3-(3,4-dichlorophenyl)diethylurea;
N-(4-isopropylphenyl)-N,N'-dimethylurea;
dichloral urea;
methyl 2-[[[[(4,6-dimethyl-2-pyrimidinyl)amino]-carbonyl] amino]sulfonyl]benzoate;
N-((6-methoxy-4-methyl-1,3,5-triazin-2-yl)aminocarbonyl)-2-(2-chloroethoxy)-benzenesulfonamide;
2-[[[(4-chloro-6-methoxypyrimidine-2-yl)aminocarbonyl] amino]-sulfonyl]benzoic acid, ethyl ester;
methyl 2-[[[[(4-methoxy-6-methyl-1,3,5-triazin-2-yl)amino] -carbonyl]amino]sulfonyl]-benzoate;
methyl 3-[[(4-methoxy-6-methyl-1,3,5-triazin-2-yl) aminocarbonyl]aminosulfonyl]-2-thio-phenecarboxylate;
methyl 2-[[[[(4,6-dimethoxypyrimidin-2-yl)amino] carbonyl]amino]sulfonyl]methyl]-benzoate;
methyl 2-[[[[(4-methoxy-6-methyl-1,3,5-triazin-2-yl) methylamino]carbonyl]amino]sulfonyl]-benzoate;

SUBSTITUTED TRIAZINES 2-chloro-4,6-bis(ethylamino)-s-triazine;
2-chloro-4-ethylamino-6-isopropylamino-s-triazine;
2-chloro-4,6-bis(3-methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-2-triazine;
2-methylmercapto-4-ethylamino-6-isopropylamino-s-triazine;
2-chloro-4,6-bis(isopropylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(t-butyl)-3-(methylthio)-1,2,4-triazine-5(4H)-one;

DIPHENYL ETHER DERIVATIVES 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-5'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1 -(3-ethoxy-4-nitrophenoxy)-4-(trifluoromethyl) benzene;
1-(carboethoxy)ethyl 5-[2-chloro-4-(trifluoromethyl)-phenoxy]-2-nitrobenzoate;
5-[2-chloro-4-(trifluoromethyl)phenoxyl]-N-(methylsulphony)-2-nitrobenzamide;

ANILIDES 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;

N-(3,4-dichlorophenyl)trimethylacetamide;
N-(3,4-dichlorophenyl)-alpha,alpha-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

OXYPHENOXY HERBICIDES 2-(4-(2,4-dichlorophenoxy)phenoxy)methyl propionate;
methyl 2-(4-(3-chloro-5-(trifluoromethyl)-2-pyridinyloxy) phenoxy)propanoate;
butyl (R)-2-[4-[5-(trifluoromethyl)-2-pyridinyloxy]-phenoxy]propionate;
ethyl 2-[4-[(6-chloro-2-benzoxazolyl)oxy]phenoxy] propanoate;
butyl 2-[4-[[5-(trifluoromethyl)-2-pyridinyl]oxy]phenoxy] propionate;
2-[4-[(6-chloro-2-quinoxalinyl)oxy]phenoxy]propionic acid, ethyl ester;

URACILS 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

NITRILES 2,6-dichlorobenzonitrile;
diphenylacetonitrile;
3,5-dibromo-4-hydroxybenzonitrile;
3,5-diiodo-4-hydroxybenzonitrile;

OTHER ORGANIC HERBICIDES 2-chloro-N,N-diallylacetamide;
N-(1,1-dimethyl-2-propynyl)-3,5-dichlorobenzamide;
maleic hydrazide;
3-amino-1,2,4-triazole; monosodium methanearsonate; disodium methanearsonate;
N,N-dimethyl-alpha,alpha-diphenylacetamidei;
N-N-di(n-propyl)-2,6-dinitro-4(trifluoromethyl)aniline;
N N-di(n-propyl)-2 6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1',c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[s-(ethylthio)propyl]-3-hydroxy-2-cyclohexen-1-one;
2-(2-chlorophenyl)methyl-4,4-dimethyl3-isoxazolidinone;
N-(1-ethylpropyl)-3,4-dimethyl-2,6-dinitrobenzamide;
4-chloro-5-(methylamino)-2-(α,α,α-trifluoro-m-toluyl)-3-(2H)-pyridazinone;
2-(3,5-dichlorophenyl)-2-(2,2,2-trichloromethyl)oxirane.

When mixtures of herbicides are employed, the relative proportions which are used will depend upon the crop to be treated and the degree of selectivity in weed control desired.

The herbicidal activity of the 2-aryl-5,6-dihydropyrimidinones of the present invention towards a number of common weeds was evaluated using a greenhouse method of testing. Using the greenhouse test methods described below, the 2-aryl-5,6-dihydropyrimidinone compounds 1-2, 4-6 and 8-15 of the present invention were evaluated for control of weeds selected from the following:

|  | Monocots |
| --- | --- |
| (BYG) | Echinochloa crus-galli |
| (FOX) | Setaria viridis |
|  | Dicots |
| (MA) | Tagetes minuta |
| (TOM) | Lycopersicon esculentum |
| (VEL) | Abutilon theophrasti. |

Seeds of selected plants were planted in flats or pots. For preemergence tests, immediately after planting, the test compound was sprayed directly onto the soil surface. The flats or pots were placed in the greenhouse and then watered. For postemergence tests, the seeds were allowed to germinate and grow for 10 to 21 days. Before application, each series of test plants was selected for uniformity, size and stage of development. The test plants were then treated with the test compound, returned to the greenhouse and watered.

The compound to be evaluated was dissolved in an appropriate solvent, usually acetone, and sprayed over the flats or pots using a carrier volume equivalent to 25 or 50 gallons per acre at the rate of application in grams per hectare (g/Ha) specified in Table IV. About two or three weeks after application of the test compound, the stage of growth of the plant was observed. Each species was evaluated on a scale of 0–100 in which 0 equals no activity and 100 equals total control.

TABLE IV

| GREENHOUSE DATA | | | | | | |
| --- | --- | --- | --- | --- | --- | --- |
| Cmpd. No. | TREAT. TYPE | g/Ha | BYG | FOX | MA | TOM | VEL |
| 1 | PRE | 1200 | 0 | 0 | 0 | 0 | 0 |
|  | POST | 1200 | 0 | 0 | 0 | 25 | 0 |
| 2 | PRE | 600 | 0 | 25 | 0 | 90 | 0 |
|  | POST | 600 | 0 | 0 | 0 | 25 | 0 |
| 4 | PRE | 1200 | 50 | 90 | 0 | 75 | 0 |
|  | POST | 1200 | 0 | 0 | 0 | 75 | 0 |
| 5 | PRE | 1200 | 0 | 75 | 0 | 75 | 0 |
|  | POST | 1200 | 0 | 0 | 0 | 25 | 0 |
| 6 | PRE | 1200 | 0 | 90 | 0 | 75 | 0 |
|  | POST | 1200 | 0 | 0 | 25 | 100 | 0 |
| 8 | PRE | 1200 | 0 | 90 | 0 | 0 | 0 |
|  | POST | 1200 | 0 | 50 | 25 | 90 | 25 |
| 9 | PRE | 1200 | 0 | 0 | 0 | 0 | 0 |
|  | POST | 1200 | 25 | 0 | 0 | 25 | 0 |
| 10 | PRE | 1200 | 50 | 90 | 25 | 75 | 0 |
|  | POST | 1200 | 25 | 0 | 25 | 75 | 25 |
| 11 | PRE | 1200 | 0 | 0 | 0 | 0 | 0 |
|  | POST | 1200 | 0 | 0 | 0 | 25 | 0 |
| 12 | PRE | 1200 | 0 | 0 | 0 | 0 | 0 |
|  | POST | 1200 | 50 | 50 | 50 | 75 | 50 |
| 13 | PRE | 1200 | 90 | 100 | 0 | 90 | 0 |
|  | POST | 1200 | 25 | 50 | 25 | 90 | 25 |
| 14 | PRE | 1200 | 100 | 100 | 90 | 100 | 100 |
|  | POST | 1200 | 50 | 50 | 25 | 100 | 50 |
| 15 | PRE | 1200 | 0 | 0 | 0 | 0 | 0 |
|  | POST | 1200 | 0 | 0 | 0 | 25 | 0 |

It is to be understood that changes and variations in this invention may be made without departing from the spirit and scope of this invention as defined by the appended claims.

We claim:
1. A compound of the formula

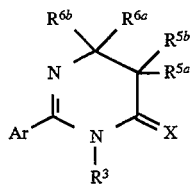

wherein

Ar is a substituted or unsubstituted aryl or heteroaryl;

$R^3$ is a haloalkyl, polyhaloalkyl, alkenyl, haloalkenyl, polyhaloalkenyl, alkynyl, haloalkynyl, polyhaloalkynyl, alkenynyl, alkoxyalkyl, haloalkoxyalkyl, oxoalkyl, trimethylsilylalkynyl or cyanoalkyl;

$R^{5a}$ and $R^{5b}$ are each independently a hydrogen atom, halo, alkyl, alkenyl, alkynyl, alkoxy, alkylthio, alkoxycarbonyl, alkoxycarbonylalkyl, haloalkyl, haloalkenyl, haloalkynyl, haloalkoxy, polyhaloalkyl, polyhaloalkenyl, polyhaloalkynyl, polyhaloalkoxy, trimethylsilylalkynyl or cyano;

$R^{6a}$ and $R^{6b}$ are each independently a hydrogen atom, halo, alkyl, alkenyl, alkynyl, alkoxy, alkylthio, haloalkylthio, alkoxyalkyl, alkoxycarbonyl, alkoxycarbonylalkyl, haloalkyl, haloalkoxy, haloalkenyl, haloalkynyl, polyhaloalkyl, polyhaloalkoxy, polyhaloalkylthio, polyhaloalkenyl, polyhaloalkynyl, cycloalkyl, aryl, aryloxy, heterocyclyl, aralkyl, alkylamino, dialkylamino, dialkylaminocarbonyl, or cyano;

$R^{5a}$ and $R^{6a}$ taken together with the carbon atoms to which they are attached may form a fused 4–7 member ring containing 2–5 methylenes; and X is an oxygen or a sulfur atom.

2. The compound of claim 1 wherein

Ar is furyl, phenyl, naphthyl, pyridyl or thienyl, or furyl, phenyl, naphthyl, pyridyl or thienyl substituted with up to three substituents independently selected from bromo, chloro, fluoro, $(C_1-C_{12})$alkyl, $cyclo(C_3-C_8)$ alkyl, $(C_2-C_{12})$alkenyl, $cyclo(C_3-C_8)$alkenyl, $(C_2-C_{12})$alkynyl, $halo(C_1-C_{12})$alkyl, polyhalo $(C_1-C_{12})$alkyl, $halo(C_2-C_{12})$alkenyl, polyhalo $(C_2-C_{12})$alkenyl, $halo(C_2-C_6)$alkynyl, polyhalo $(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, $phen(C_1-C_{12})$alkyl, $phen(C_2-C_{12})$alkenyl, phen $(C_2-C_{12})$alkynyl, cyano, $halo(C_1-C_{12})$alkoxy, 1,3-dioxalan-2-yl, hydroxyimino, $polyhalo(C_1-C_{12})$alkoxy and nitro;

$R^3$ is $halo(C_1-C_3)$alkyl, $polyhalo(C_1-C_3)$alkyl, $(C_3-C_4)$ alkenyl, $halo(C_3-C_4)$alkenyl, $polyhalo(C_3-C_4)$alkenyl, $(C_3-C_6)$alkynyl, $halo(C_3-C_6)$alkynyl, $polyhalo(C_3-C_6)$ alkynyl, $(C_5-C_6)$alkenynyl, $(C_1-C_6)$alkoxy$(C_1-C_6)$ alkyl, $halo(C_1-C_6)$alkoxy$(C_1-C_6)$alkyl, 2-oxo$(C_2-C_3)$ alkyl, trimethylsilyl$(C_3-C_4)$alkynyl or cyano$(C_1-C_6)$ alkyl;

$R^{5a}$ and $R^{5b}$ are each independently a hydrogen atom, $(C_1-C_6)$alkyl, $(C_2-C_6)$alkenyl, $(C_2-C_6)$alkynyl, trimethylsilyl$(C_2-C_3)$alkynyl, $(C_1-C_6)$alkoxy, halo $(C_1-C_6)$alkyl, $polyhalo(C_1-C_6)$alkyl, $halo(C_2-C_6)$ alkenyl, $polyhalo(C_2-C_6)$alkenyl, $halo(C_2-C_6)$alkynyl, $polyhalo(C_2-C_6)$alkynyl, $halo(C_1-C_6)$alkoxy, polyhalo $(C_1-C_6)$alkoxy, $(C_1-C_6)$alkoxycarbonyl, $(C_1-C_3)$ alkoxycarbonyl$(C_1-C_3)$alkyl, $(C_1-C_6)$alkylthio, halo or cyano;

$R^{6a}$ and $R^{6b}$ are each independently a hydrogen atom, halo, $(C_1-C_3)$alkyl, $(C_2-C_6)$alkenyl, $(C_2-C_6)$alkynyl, $halo(C_1-C_6)$alkyl or $polyhalo(C_1-C_6)$alkyl, halo $(C_2-C_6)$alkenyl or $polyhalo(C_2-C_6)$alkenyl, halo $(C_2-C_6)$alkynyl or $polyhalo(C_2-C_6)$alkynyl, $(C_1-C_6)$ alkoxy$(C_1-C_4)$alkyl, $(C_1-C_6)$alkoxy, $(C_1-C_6)$alkylthio, $C_1-C_3)$alkoxycarbonyl, $(C_1-C_3)$alkoxycarbonyl $(C_1-C_3)$alkyl, $cyclo(C_3-C_7)$alkyl, $halo(C_1-C_6)$ alkylthio, $polyhalo(C_1-C_6)$alkythio, $halo(C_1-C_6)$ alkoxy, $polyhalo(C_1-C_6)$alkoxy, $(C_4-C_5)$heterocyclyl, $(C_1-C_3)$alkylamino, $di(C_1-C_3)$alkylamino, $di(C_1-C_3)$ alkylaminocarbonyl, cyano, aryl, aryloxy, $ar(C_1-C_4)$ alkyl, or aryl, aryloxy or $ar(C_1-C_4)$alkyl substituted on the aryl ring with up to three substituents independently selected from the group consisting of halo, $(C_1-C_6)$ alkyl, $cyclo(C_5-C_6)$alkyl, $(C_2-C_6)$alkenyl, cyclo $(C_3-C_8)$alkenyl, $(C_2-C_6)$alkynyl, $halo(C_1-C_6)$alkyl, $polyhalo(C_1-C_6)$alkyl, $halo(C_2-C_6)$alkenyl, polyhalo $(C_2-C_6)$alkenyl, $halo(C_2-C_6)$alkynyl, $polyhalo(C_2-C_6)$ alkynyl, $(C_1-C_6)$alkoxy, $(C_1-C_6)$alkylthio, $C_1-C_6)$ alkylsulfonyl, $(C_1-C_6)$alkylsulfinyl, phenyl, phen $(C_1-C_6)$alkyl, $phen(C_2-C_6)$alkenyl, $phen(C_2-C_6)$ alkynyl, cyano, $halo(C_1-C_6)$alkoxy, 1,3-dioxalan-2-yl, hydroxyimino and nitro; and X is an oxygen atom.

3. The compound of claim 2 wherein Ar is phenyl, 3-methylphenyl, 3methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)phenyl, 3-(hydroxyimino)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, and 3,4,5-trifluorophenyl, 6-chloro-2-pyridyl, 3-pyridyl, 5-bromo-3-pyridyl, 5,6-dichloro-3-pyridyl, 5-chloro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4-pyridyl, 2,6-dichloro-4-pyridyl, 2-furyl, 3-furyl, 2-naphthyl, 2-thienyl, 3-thienyl, 4-chloro-2-thienyl, 5-chloro-2-thienyl, 5-chloro-3-thienyl or 2,5-dichloro-3-thienyl.

4. The compound of claim 3 wherein Ar is phenyl, 3-fluorophenyl, 3,5-difluorophenyl, 3,5-dichlorophenyl, 3-chlorophenyl, 2-chloro-4-pyridyl, 2-fluoro-4pyridyl, 5-chloro-3-pyridyl, 2,6-dichloro-4-pyridyl or 5-chloro-3-thienyl.

5. The compound of claim 2 wherein $R^3$ is allyl, 3-chloroallyl, pentynyl, propargyl, 2-butynyl, iodopropargyl, bromopropargyl, methoxymethyl, 2-methoxyethyl, acetonyl, 3-(trimethylsilyl)propargyl, pent-4-en-2-ynyl or cyanomethyl.

6. The compound of claim 5 wherein $R^3$ is 2-pentynyl, propargyl, 2-butynyl, iodopropargyl or methoxymethyl.

7. The compound of claim 2 wherein $R^{5a}$ and $R^{5b}$ are each independently a hydrogen atom, methyl, ethyl, n-propyl, isopropyl, propargyl, methoxy, methylthio, methoxycarbonylmethyl, allyl, fluoromethyl, trifluoromethyl, difluoromethoxy, trifluoromethoxy, chloro and fluoro.

8. The compound of claim 7 wherein $R^{5a}$ and $R^{5b}$ are each independently a hydrogen atom, methyl, ethyl, methoxycarbonyl, ethoxycarbonyl, allyl or propargyl.

9. The compound of claim 2 wherein $R^{6a}$ and $R^{6b}$ are each independently a hydrogen atom, phenyl, phenyl substituted with up to two substituents independently selected from halo, methyl, ethyl and trifluoromethyl, methyl, ethyl, n-propyl, isopropyl, n-butyl, 2-methyl-1-propenyl, allyl, 3-thienyl, 3-furyl, 2-thienyl, 4-pyridyl, methoxy, ethoxy, ethoxycarbonyl, but-2-ynyl, but-3-ynyl, propargyl, fluoro, bromo, chloro, trifluoromethyl, pentafluoroethyl, trichloromethyl, bromomethyl, chloromethyl, difluoromethyl, chlorodifluoromethyl, difluoromethoxy, trifluoromethoxy, methylthio, methoxymethyl, benzyl, cyclopropyl, cyclobutyl, cyclopentyl, dimethylamino or dimethylaminocarbonyl.

10. The compound of claim 9 wherein $R^{6a}$ and $R^{6b}$ are each independently a hydrogen atom, phenyl, methyl, ethyl, n-propyl, isopropyl, trifluoromethyl, difluoromethyl, chlorodifluoromethyl, allyl or propargyl.

11. A herbicidal composition comprising a compound of the formula

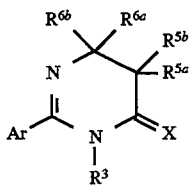

wherein

Ar is a substituted or unsubstituted aryl or heteroaryl;

$R^3$ is an alkyl, haloalkyl, polyhaloalkyl, alkenyl, haloalkenyl, polyhaloalkenyl, alkynyl, haloalkynyl, polyhaloalkynyl, alkenynyl, alkoxyalkyl, dialkoxyalkyl, haloalkoxyalkyl, oxoalkyl, trimethylsilylalkynyl or cyanoalkyl;

$R^{5a}$ and $R^{5b}$ are each independently a hydrogen atom, halo, alkyl, alkenyl, alkynyl, alkoxy, alkylthio, alkoxycarbonyl, alkoxycarbonylalkyl, haloalkyl, haloalkenyl, haloalkynyl, haloalkoxy, polyhaloalkyl, polyhaloalkenyl, polyhaloalkynyl, polyhaloalkoxy, trimethylsilylalkynyl or cyano;

$R^{6a}$ and $R^{6b}$ are each independently a hydrogen atom, halo, alkyl, alkenyl, alkynyl, alkoxy, alkylthio, haloalkylthio, alkoxyalkyl, alkoxycarbonyl, alkoxycarbonylalkyl, haloalkyl, haloalkoxy, haloalkenyl, haloalkynyl, polyhaloalkyl, polyhaloalkoxy, polyhaloalkylthio, polyhaloalkenyl, polyhaloalkynyl, cycloalkyl, aryl, aryloxy, heterocyclyl, aralkyl, alkylamino, dialkylamino, dialkylaminocarbonyl, or cyano;

$R^{5a}$ and $R^{6a}$ taken together with the carbon atoms to which they are attached may form a fused 4–7 member ring containing 2–5 methylenes;

X is an oxygen or a sulfur atom; and an agronomically acceptable carrier.

12. The composition of claim 11 wherein

Ar is furyl, phenyl, naphthyl, pyridyl or thienyl, or furyl, phenyl, naphthyl, pyridyl or thienyl substituted with up to three substituents independently selected from bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo $(C_2-C_{12})$alkenyl, halo$(C_2-C_6)$alkynyl, polyhalo $(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen $(C_2-C_{12})$alkynyl, cyano, halo$(C_1-C_{12})$alkoxy, 1,3-dioxalan-2-yl, hydroxyimino, polyhalo$(C_1-C_{12})$alkoxy and nitro;

$R^3$ is $(C_1-C_3)$alkyl, halo$(C_1-C_3)$alkyl, polyhalo$(C_1-C_3)$ alkyl, $(C_3-C_4)$alkenyl, halo$(C_3-C_4)$alkenyl, polyhalo $(C_3-C_4)$alkenyl, $(C_3-C_6)$alkynyl, halo$(C_3-C_6)$alkynyl, polyhalo$(C_3-C_6)$alkynyl, $(C_5-C_6)$alkenynyl, $(C_1-C_6)$ alkoxy$(C_1-C_6)$alkyl, di$(C_1-C_6)$alkoxy$(C_1-C_6)$alkyl, halo$(C_1C_6)$alkoxy$(C_1-C_6)$alkyl, 2-oxo$(C_2-C_3)$alkyl, trimethylsilyl$(C_3-C_4)$alkynyl or cyano$(C_1-C_6)$alkyl;

$R^{5a}$ and $R^{5b}$ are each independently a hydrogen atom, $(C_1-C_6)$alkyl, $(C_2C_6)$alkenyl, $(C_2-C_6)$alkynyl, trimethylsilyl$(C_2-C_3)$alkynyl, $(C_1-C_6)$alkoxy, halo $(C_1-C_6)$alkyl, polyhalo$(C_1-C_6)$alkyl, halo$(C_2-C_6)$ alkenyl, polyhalo$(C_2-C_6)$alkenyl, halo$(C_2-C_6)$alkynyl, polyhalo$(C_2-C_6)$alkynyl, halo$(C_1-C_6)$alkoxy, polyhalo $(C_1-C_6)$alkoxy, $(C_1-C_6)$alkoxycarbonyl, $(C_1-C_3)$ alkoxycarbonyl$(C_1-C_3)$alkyl, $C_1-C_6)$alkylthio, halo or cyano;

$R^{6a}$ and $R^{6b}$ are each independently a hydrogen atom, halo, $(C_1-C_8)$alkyl, $(C_2-C_6)$alkenyl, $(C_2-C_6)$alkynyl, halo$(C_1-C_6)$alkyl or polyhalo$(C_1-C_6)$alkyl, halo $(C_2-C_6)$alkenyl or polyhalo$(C_2-C_6)$alkenyl, halo $(C_2-C_6)$alkynyl or polyhalo$(C_2C_6)$alkynyl, $(C_1-C_6)$ alkoxy$(C_1-C_4)$alkyl, $(C_1-C_6)$alkoxy, $(C_1-C_6)$alkylthio, $C_1-C_3)$alkoxycarbonyl, $(C_1-C_3)$alkoxycarbonyl $(C_1-C_3)$alkyl, cyclo$(C_3-C_7)$alkyl, halo$(C_1-C_6)$ alkylthio, polyhalo$(C_1-C_6)$alkythio, halo$(C_1-C_6)$ alkoxy, polyhalo$(C_1-C_6)$alkoxy, $(C_4-C_5)$heterocyclyl, $(C_1-C_3)$alkylamino, di$(C_1-C_3)$alkylamino, di$(C_1-C_3)$ alkylaminocarbonyl, cyano, aryl, aryloxy, ar$(C_1-C_4)$ alkyl, or aryl, aryloxy or ar$(C_1-C_4)$alkyl substituted on the aryl ring with up to three substituents independently selected from the group consisting of halo, $(C_1-C_6)$ alkyl, cyclo$(C_5-C_6)$alkyl, $(C_2-C_6)$alkenyl, cyclo $(C_3-C_8)$alkenyl, $(C_2-C_6)$alkynyl, halo$(C_1-C_6)$alkyl, polyhalo$(C_1-C_6)$alkyl, halo$(C_2-C_6)$alkenyl, polyhalo $(C_2-C_6)$alkenyl, halo$(C_2C_6)$alkynyl, polyhalo$(C_2-C_6)$ alkynyl, $(C_1-C_6)$alkoxy, $(C_1-C_6)$alkylthio, $(C_1-C_6)$ alkylsulfonyl, $(C_1-C_6)$alkylsulfinyl, phenyl, phen $(C_1-C_6)$alkyl, phen$(C_2C_6)$alkenyl, phen$(C_2-C_6)$ alkynyl, cyano, halo$(C_1-C_6)$alkoxy, 1,3-dioxalan-2-yl, hydroxyimino and nitro; and X is an oxygen atom.

13. The composition of claim 12 wherein Ar is phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)phenyl, 3-(hydroxyimino)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, and 3,4,5-trifluorophenyl 6-chloro-2-pyridyl, 3-pyridyl, 5-bromo-3-pyridyl, 5,6-dichloro-3-pyridyl, 5-chloro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4-pyridyl, 2,6-dichloro-4-pyridyl, 2-furyl. 3-furyl, 2-naphthyl, 2-thienyl, 3-thienyl, 4-chloro-2-thienyl, 5-chloro-2-thienyl, 5-chloro-3-thienyl or 2,5-dichloro-3-thienyl.

14. The composition of claim 13 wherein Ar is phenyl, 3-fluorophenyl, 3,5-difluorophenyl, 3,5-dichlorophenyl, 3-chlorophenyl, 2-chloro-4-pyridyl, 2-fluoro-4-pyridyl, 5-chloro-3-pyridyl, 2,6-dichloro-4-pyridyl or 5-chloro-3-thienyl.

15. The composition of claim 12 wherein $R^3$ is ethyl, allyl, 3-chloroallyl, pentynyl, propargyl, 2-butynyl, iodopropargyl, bromopropargyl, methoxymethyl, 2-methoxyethyl, 2,2-dimethoxypropyl, acetonyl, 3-(trimethylsilyl)propargyl, pent-4-en-2-ynyl or cyanomethyl.

16. The composition of claim 15 wherein $R^3$ is 2-pentynyl, propargyl, 2-butynyl, iodopropargyl or methoxymethyl.

17. The composition of claim 12 wherein $R^{5a}$ and $R^{5b}$ are each independently a hydrogen atom, methyl, ethyl, n-propyl, isopropyl, propargyl, methoxy, methylthio, methoxycarbonylmethyl, allyl, fluoromethyl, trifluoromethyl, difluoromethoxy, trifluoromethoxy, chloro and fluoro.

18. The composition of claim 17 wherein $R^{5a}$ and $R^{5b}$ are each independently a hydrogen atom, methyl, ethyl, methoxycarbonyl, ethoxycarbonyl, allyl or propargyl.

19. The composition of claim 12 wherein $R^{6a}$ and $R^{6b}$ are each independently a hydrogen atom, phenyl, phenyl substituted with up to two substituents independently selected from halo, methyl, ethyl and trifluoromethyl, methyl, ethyl, n-propyl, isopropyl, n-butyl, 2-methyl-1-propenyl, allyl, 3-thienyl, 3-furyl, 2-thienyl, 4-pyridyl, methoxy, ethoxy, ethoxycarbonyl, but-2-ynyl, but-3-ynyl, propargyl, fluoro, bromo, chloro, trifluoromethyl, pentafluoroethyl, trichloromethyl, bromomethyl, chloromethyl, difluoromethyl, chlorodifluoromethyl, difluoromethoxy, trifluoromethoxy, methylthio, methoxymethyl, benzyl, cyclopropyl, cyclobutyl, cyclopentyl, dimethylamino or dimethylaminocarbonyl.

20. The composition of claim 19 wherein $R^{6a}$ and $R^{6b}$ are each independently a hydrogen atom, phenyl, methyl, ethyl, n-propyl, isopropyl, trifluoromethyl, difluoromethyl, chlorodifluoromethyl, allyl or propargyl.

21. A method of controlling a weed comprising applying a herbicidally effective amount of a composition of claims 11 or 12 to the weed, to the locus of the weed or to the growth medium of the weed.

22. The compound of claims 1 or 2 which is 2-(3-chlorophenyl)-3-propargyl-6-trifluoromethyl-5,6-dihydropyrimidin-4-one, 2-(3,5-dichlorophenyl)-3-propargyl-6-trifluoromethyl-5,6-dihydropyrimidin-4-one or 5-ethyl-2-phenyl-3-propargyl-6-trifluoromethyl-5,6-dihydropyrimidin-4-one.

\* \* \* \* \*